US008841382B2

(12) United States Patent
Cristadoro et al.

(10) Patent No.: US 8,841,382 B2
(45) Date of Patent: Sep. 23, 2014

(54) HYPERBRANCHED POLYETHERS/DENDRIMERS FOR SOLUBILZATION OF SPARINGLY SOLUBLE ACTIVE INGREDIENTS

(75) Inventors: Anna Cristadoro, Heppenheim (DE); Holger Türk, Mannheim (DE); Michael Ishaque, Mannheim (DE); Rabie Al-Hellani, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 2 days.

(21) Appl. No.: 13/222,550

(22) Filed: Aug. 31, 2011

(65) Prior Publication Data
US 2012/0053057 A1 Mar. 1, 2012

Related U.S. Application Data

(60) Provisional application No. 61/378,951, filed on Sep. 1, 2010.

(51) Int. Cl.
| | |
|---|---|
| *C08G 65/00* | (2006.01) |
| *A01N 25/04* | (2006.01) |
| *C07F 9/09* | (2006.01) |
| *A01N 25/30* | (2006.01) |
| C08G 65/34 | (2006.01) |
| C08L 71/00 | (2006.01) |
| A01N 25/00 | (2006.01) |
| A01N 31/00 | (2006.01) |

(52) U.S. Cl.
CPC ............... *C07F 9/091* (2013.01); *A01N 25/04* (2013.01); *A01N 25/30* (2013.01); *Y10S 424/16* (2013.01)
USPC .......... 525/54.1; 525/175; 525/176; 525/360; 525/410; 525/419; 525/437; 525/440.01; 525/440.15; 528/310; 528/328; 528/332; 528/350; 528/363; 528/373; 528/417; 528/422; 528/451; 514/785; 514/788; 424/DIG. 16

(58) Field of Classification Search
CPC ........ C08G 65/00; C08G 65/34; C08L 71/00; A01N 25/00; A01N 31/00
USPC ......... 528/332, 310, 328, 350, 363, 373, 417, 528/422, 451; 525/54.1, 175, 176, 360, 525/410, 419, 437, 440.01, 440.15; 424/DIG. 16; 514/785, 788
See application file for complete search history.

(56) References Cited

U.S. PATENT DOCUMENTS

| | | | |
|---|---|---|---|
| 5,807,971 A * | 9/1998 | Gozzini et al. ................ 528/332 |
| 2005/0131205 A1 * | 6/2005 | Hggman et al. ............... 528/417 |
| 2006/0178475 A1 | 8/2006 | Bentley et al. | |
| 2002/0229972 | 9/2008 | Blease et al. | |

FOREIGN PATENT DOCUMENTS

| | | |
|---|---|---|
| EP | 2 100 621 | 9/2009 |
| WO | WO 2010/000713 | 1/2010 |

OTHER PUBLICATIONS

Magnusson et al., "Synthesis of hyperbranched aliphatic polyethers via cationic ring-opening polymerization of 3-ethyl-3(hydroxymethyl)oxetane," 1999, Macromol. Rapid Comm., 20(8):453-457.*

International Search Report and Written Opinion dated Nov. 23, 2011, prepared in International Application No. PCT/IB2011/053818, filed Aug. 31, 2011.

Grayson, S. et al., "Synthesis and surface functionalization of aliphatic polyether dendrons", J. Am. Chem. Soc. (2000), pp. 10335-10344, vol. 122.

Jayaraman, M. et al., "A convergent route to novel aliphatic polyether dendrimers", J. Am. Chem. Soc. (1998), pp. 12996-12997, vol. 120.

Richter, A. et al., "Non-ionic dendritic glycerol-based amphiphiles: Novel excipients for the solubilization of poorly water-soluble anticancer drug Sagopilone", European Journal of Pharmaceutical Sciences, (2010), pp. 48-55, vol. 40.

* cited by examiner

*Primary Examiner* — Jane C Oswecki
(74) *Attorney, Agent, or Firm* — Brinks Gilson & Lione

(57) ABSTRACT

The present invention provides an amphiphile of the formula (I) as described hereinafter. The invention further relates to a process for preparing the amphiphile and to a composition comprising the amphiphile and a sparingly water-soluble active ingredient. It further relates to a process for producing the composition by contacting the amphiphile and the active ingredient, and to the use of the amphiphile for solubilizing a sparingly water-soluble active ingredient in aqueous solutions. The invention also relates to the use of the amphiphile in an agrochemical formulation comprising the amphiphile and a pesticide for controlling phytopathogenic fungi and/or unwanted vegetation and/or unwanted insect or mite infestation and/or for regulating the growth of plants, and finally to plant propagation material comprising the amphiphile.

8 Claims, No Drawings

HYPERBRANCHED POLYETHERS/DENDRIMERS FOR SOLUBILZATION OF SPARINGLY SOLUBLE ACTIVE INGREDIENTS

This application claims the benefit of U.S. Provisional Application No. 61/378,951 filed Sep. 1, 2010, the entire contents of which are hereby incorporated herein by reference.

The present invention provides an amphiphile of the formula (I) as described hereinafter. The invention further relates to a process for preparing the amphiphile and to a composition comprising the amphiphile and a sparingly water-soluble active ingredient. It further relates to a process for producing the composition by contacting the amphiphile and the active ingredient, and to the use of the amphiphile for solubilizing a sparingly water-soluble active ingredient in aqueous solutions. The invention also relates to the use of the amphiphile in an agrochemical formulation comprising the amphiphile and a pesticide for controlling phytopathogenic fungi and/or unwanted vegetation and/or unwanted insect or mite infestation and/or for regulating the growth of plants, and finally to plant propagation material comprising the amphiphile. Combinations of preferred features with other preferred features are encompassed by the present invention.

In many cases, it is necessary to solubilize hydrophobic active ingredients in water without chemically altering the active ingredient in question as such. For this purpose, it is possible, for example, to prepare an emulsion, in which case the active ingredient in question is present in the oil phase of the emulsion. However for many active pharmaceutical ingredients, or in particular crop protection compositions, especially for those which are to be transported with a body fluid or in a plant's sap, an approach of this kind is not possible. Emulsions can break under the action of high shear forces. Moreover, sterilization, for example for active pharmaceutical ingredients, while maintaining the emulsion is not possible in many cases.

Hyperbranched polyethers and processes for preparation and modification are common knowledge:

WO 2010/000713 discloses linear dendritic polyglycerol compounds and preparation thereof by means of a "CLICK reaction" (1,3-dipolar cycloaddition of alkyne and azide to form a triazole ring). These compounds can be used to solubilize hydrophobic substances.

EP 2 100 621 discloses linear dendritic polyglycerol compounds and preparation thereof by means of a "CLICK reaction".

Grayson and Fréchet (J. Am. Chem. Soc. 2000, 122, 10335-10344) disclose the synthesis and functionalization of aliphatic polyether dendrons.

Jayaraman and Fréchet (J. Am. Chem. Soc. 1998, 120, 12996-12997) disclose the synthesis of aliphatic polyether dendrimers and the silylation of the focal hydroxyl group.

Richter et al. (Europ. J. Pharm. Sci. 2010, 40 (1), 48-55) disclose the preparation of nonionic dendritic glycerol-based amphiphiles by means of a "CLICK reaction".

A disadvantage of the known hyperbranched polyethers and the preparation processes therefor is that they require very costly reactants, especially for the CLICK reaction. It was therefore not possible to employ the known preparation processes industrially. A further disadvantage was that the known amphiphiles can solubilize only small amounts of sparingly soluble active ingredients, since they do not usually possess a markedly amphiphilic structure. A further disadvantage is that only anionic groups are described as polar end groups. However, anionic groups are undesired in formulations comprising active ingredients, since there are often undesired interactions, for example with cationic active ingredients. A further disadvantage is that the polarity of the amphiphiles can be adjusted only very roughly, for example by exchanging one anionic end group for another kind of anionic end group.

It was an object of the present invention to overcome the aforementioned disadvantages. In addition, the intention was to find a simple preparation process based on industrially available reactants. The process was to make the amphiphile available in high yields and with as few purification steps as possible. The amphiphile thus prepared was to make available high concentrations of sparingly soluble active ingredients, such as pesticides, in aqueous solutions.

The object is achieved by an amphiphile of the formula (I)

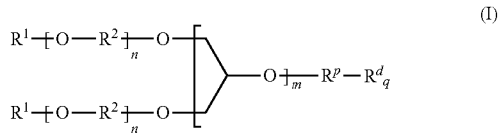

where
$R^1$: each independently H, $C_1$-$C_{10}$-alkyl, $-SO_3^-$, $-PO_3^{2-}$, $-COO^-$, $-R'-SO_3^-$, $-R'-PO_3^{2-}$, or $-R'-CO_2^-$, where R' is $C_1$-$C_{12}$-alkylene;
$R^2$: each independently $C_2$-$C_5$-alkylene, where at least 50 mol % of $C_2$-alkylene is present in respect of $R^2$;
n: 1 to 200;
m: 1 to 6;
q: 0 to 50;
$R^p$: a nonpolar polymer $R^{np}$ or a polar polymer $R^{pp}$; and
$R^d$: a nonpolar dendron $R^{nd}$ or a polar dendron $R^{pd}$.

$R^1$ is preferably independently H or $C_1$-$C_{10}$-alkyl. $R^1$ is more preferably H or $C_1$-$C_6$-alkyl.

$R^1$ is most preferably H or methyl, especially methyl. R' is preferably $C_2$-$C_6$-alkylene.

$R^2$ is preferably independently ethylene, propylene, or a mixture of ethylene and propylene. The alkylene radicals of $R^2$ may be present individually or in mixtures of a plurality of different alkylene radicals. For example, ethylene and propylene radicals may be mixed. The different alkylene radicals may be present in random sequence or in block form.

n is preferably 2 to 100, more preferably 4 to 50 and most preferably 8 to 40.

m is preferably 2 to 5 and more preferably 3 to 4.

q is preferably 0 to 20, more preferably 0 to 5 and especially zero or one. In a further preferred embodiment q is zero. In a further preferred embodiment, q is at least 1, more preferably exactly 1. In a further preferred embodiment q is from 2 to 20.

$R^p$ denotes a radical with at least one unoccupied bonding site, through which $R^p$ is bonded to the oxygen of the structural unit (V). When q is greater than or equal to 1, $R^p$ denotes a radical having at least two unoccupied bonding sites. In this case, one bonding site, as described, is to the oxygen of (V), and the further unoccupied bonding site is to the $R^d$ radical(s). $R^p$ is preferably a nonpolar polymer or a nonpolar radical $R^{np}$. In a specific embodiment, $R^p$ may also be a mixture of different radicals.

$R^d$ is a nonpolar dendron $R^{nd}$ or a polar dendron $R^{pd}$. Typically $R^d$ is a radical having at least one unoccupied bonding site, through which $R^d$ is bonded to $R^p$. The bond of $R^d$ to $R^p$ may be at the end or at any other position in the polymer chain of $R^p$. $R^d$ is preferably a nonpolar dendron $R^{nd}$. In a further embodiment, $R^d$ is preferably a nonpolar dendron $R^{nd}$ if $R^p$ is a polar polymer $R^{pp}$. In a specific embodiment, $R^d$ may also be a mixture of different dendrons.

The amphiphile of the formula (I) comprises a group of the formula (V)

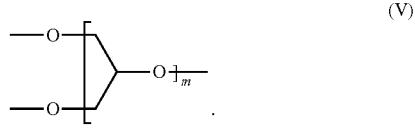

This structural unit (V) may be a dendrimer or a hyperbranched polymer. The structural unit (V) is preferably a dendrimer. Such a dendrimer typically has only perfectly branched units with no defects. It is especially preferred that the structural unit (V) is a mixture of different dendrimers of different generations, expressed by different parameters m. Further suitable and preferred embodiments of this structure are as described for the polar dendron of the formula (IV).

Suitable nonpolar $R^{np}$ are selected from

NPa) —C(O)(CHR$^a$)$_2$—CO$_2$H, where $R^a$ is independently H, $C_4$-$C_{44}$-alkyl, $C_4$-$C_{44}$-alkenyl, $C_6$-$C_{44}$-aryl, $C_7$-$C_{44}$-aralkyl or $C_7$-$C_{44}$-alkylaryl, and where at most one of the two $R^a$ radicals is hydrogen;

NPb) —C(O)(CHR$^b$)$_2$—CO$_2$H, where $R^b$ is independently hydrogen or a poly($C_{2-12}$-alkylene) group, which may optionally comprise at least one carboxylic acid group, a carboxylic anhydride group or an $R^d$ radical bonded via a carboxylic ester group and where at most one of the two $R^b$ radicals is hydrogen;

NPc) a polymer comprising a nonpolar, ethylenically unsaturated monomer;

NPd) a polymer comprising poly($C_{2-5}$-alkylene oxide), where up to 50 mol % of the $C_{2-5}$-alkylene oxide groups are ethylene oxide;

NPe) a polymer comprising poly(caprolactone);

NPf) a polycondensate from the group of the polyurethanes, polyesterpolyurethanes, polyetherpolyurethanes, polycarbonates, polyesters and polyamides, where the monomeric units present are poly($C_{3-5}$-alkylene oxide) and/or a polycondensable monomer having at least five carbon atoms; or NPg) a nonpolar dendrimer or nonpolar, hyperbranched polymer.

The nonpolar polymer $R^{np}$ is preferably selected from NPa or NPb. In a further preferred embodiment $R^{np}$ is NPa. In a further preferred embodiment, $R^{np}$ is NPb.

Preferred nonpolar polymers NPa are radicals —C(O)(CHR$^a$)$_2$—CO$_2$H, where $R^a$ is independently H, $C_8$-$C_{44}$-alkyl, $C_8$-$C_{44}$-alkenyl, and where at most one of the two $R^a$ radicals is hydrogen. Particularly preferred NPa are —C(O)(CHR$^a$)$_2$—CO$_2$H radicals, where $R^a$ is independently H, $C_{14}$-$C_{32}$-alkyl, $C_{14}$-$C_{32}$-alkenyl, and where at most one of the two $R^a$ radicals is hydrogen. Such NPa radicals are typically joined to the focal hydroxyl group by the reaction thereof with an aliphatic carboxylic anhydride, such as alkenylsuccinic anhydride.

Preferred nonpolar polymers NPb are the —C(O)(CHR$^b$)$_2$—CO$_2$H radicals, where $R^b$ is independently hydrogen or a poly($C_{2-6}$-alkylene) group, and where at most one of the two $R^b$ radicals is hydrogen. The poly($C_{2-6}$-alkylene) radical is preferably a polyethylene, polypropylene, polybutylene, or polyisobutylene radical, especially a polybutylene or polyisobutylene radical. The number-average molar mass may be in the range from 300 to 20 000 g/mol. Such NPb radicals are typically joined to the focal hydroxyl group by the reaction thereof with a carboxylic anhydride-terminated poly($C_{2-12}$-alkylene), such as polyisobutylenesuccinic anhydride.

Preferred nonpolar polymers NPc are polymers comprising a nonpolar, ethylenically unsaturated monomer, which is selected from $C_1$-$C_{20}$-alkyl(meth)acrylates or vinylaromatics having up to 20 carbon atoms. The nonpolar polymer NPc may comprise at least one nonpolar, ethylenically unsaturated monomer. Examples comprise methyl(meth)acrylate, ethyl(meth)acrylate, n-butyl(meth)acrylate, 2-ethylhexyl(meth)acrylate, lauryl(meth)acrylate, stearyl(meth)acrylate or 4-t-butylcyclohexyl(meth)acrylate. Examples of useful vinylaromatic compounds include vinyltoluene, α-butylstyrene, 4-n-butylstyrene, 4-n-decylstyrene or styrene. The monomers are normally present in polymerized form in the polymer. The proportion of nonpolar monomers is preferably at least 50 mol %, more preferably at least 70 mol %, in relation to all polymerized monomers of NPc. The nonpolar polymer may be in the form of a homopolymer or random or block copolymer. The number-average molar mass is usually in the range from 500 to 50 000 g/mol, preferably from 500 to 20 000 g/mol and more preferably from 1000 to 10 000 g/mol. The nonpolar polymer usually comprises at least one functional end group, such as an alcohol, acid, amine or ester group. The functional end group is preferably introduced by means of a functional initiator or regulator. Such polymers NPc are typically joined to the focal hydroxyl group by the direct reaction thereof with the functional end group or via a low molecular weight linker as described hereinafter.

Preferred nonpolar polymers NPd are polymers comprising poly($C_{2-5}$-alkylene oxide), where up to 50 mol % of the $C_{2-5}$-alkylene oxide groups are ethylene oxide. The polymer may take the form of a homopolymer or block polymer. The number average molar mass is usually in the range from 300 to 20 000 g/mol, preferably from 300 to 10 000 g/mol and more preferably from 500 to 5000 g/mol (measured by means of GPC, in dimethylacetamide with polymethyl methacrylate (PMMA) as the standard). Such polymers NPd are typically joined to the focal hydroxyl group via a low molecular weight linker, as described hereinafter.

Preferred nonpolar polymers NPe are polymers comprising poly(caprolactone), where at least 50 mol % of NPe are poly(caprolactone), based on NPe. NPe may take the form of a block polymer or a homopolymer. The number average molar mass is usually in the range from 114 to 50 000 g/mol, more preferably 114 to 20 000 g/mol. Such polymers NPe are typically joined to the focal hydroxyl group by ring-opening polymerization or via a low molecular weight linker, as described hereinafter.

Preferred nonpolar polymers NPf are polycondensates from the group of the polyurethanes, polyesterpolyurethanes, polyetherpolyurethanes, polycarbonates, polyesters and polyamides, where the monomeric units present are poly($C_{3-5}$-alkylene oxide), preferably polypropylene oxide and/or at least one polycondensable monomer having at least five (preferably at least six) carbon atoms. Examples of polycondensable monomers are diacids, diisocyanates, diamines, and diesters. Particularly preferred examples of polycondensable monomers are glutaric acid, adipic acid, sebacic acid, hexamethylene diisocyanate, isophorone diisocyanate, 1,6-hexanediol, cyclohexanedimethanol, 1,6-hexamethylenediamine or 1,8-octamethylenediamine. The number-average molar mass is usually in the range from 300 to 10 000 g/mol, preferably from 300 to 5000 g/mol and more preferably from 500 to 2000 g/mol. Such polymers NPf are typically joined to the focal hydroxyl group by the direct reaction thereof with the functional end group or via a low molecular weight linker, as described hereinafter.

Preferred nonpolar polymers NPg are hyperbranched polyureas, hyperbranched polycarbonates and hyperbranched polyesters based on a hydrophobic dicarboxylic acid and a trifunctional alcohol.

A hyperbranched polyurea is common knowledge, for example from the pending EP 09177370.5. It is preferably obtainable by a process comprising the reaction of a blocked di- or polyisocyanate with at least one at least difunctional primary and/or secondary amine with elimination of the blocking agent to give the polyurea. The term "polyurea" in the context of the present invention comprises polymers which, in addition to urea groups, may also have urethane groups, allophanate groups, biuret groups and further functional groups, for example amine functions. The urethane groups are usually O-alkylurethane groups, where the alkyl radical has one to 18 carbon atoms. The O-alkylurethane groups are preferably obtainable by reaction of an isocyanate group with a monoalcohol, which has been used as a blocking agent.

A hyperbranched polycarbonate is common knowledge, for example from the pending PCT/EP2010/056001. It is preferably obtainable by a) preparing a condensation product (K) by reaction of an organic carbonate (A) or of a phosgene derivative with an alcohol (B1), which has at least three hydroxyl groups, and b) intermolecular conversion of K to the hyperbranched polycarbonate, where the ratio of the OH groups to the carbonate or phosgene groups is selected such that K has an average of either i) one carbonate or carbamoyl chloride group and more than one OH group, or ii) one OH group and more than one carbonate or carbamoyl group. Preference is given to using aliphatic carbonates as the organic carbonate (A), especially those in which the radicals comprise 1 to 5 carbon atoms, for example dimethyl carbonate, diethyl carbonate, di-n-propyl carbonate, di-n-butyl carbonate or diisobutyl carbonate. Diethyl carbonate is especially preferred. Examples of alcohols (B1) having at least three OH groups comprise glycerol, trimethylolmethane, trimethylolethane, trimethylolpropane, trimethylolbutane, 1,2,4-butanetriol, 1,2,3-hexanetriol, 1,2,4-hexanetriol, tris(hydroxymethyl)amine, tris(hydroxyethyl)amine, tris(hydroxypropyl)amine, pentaerythritol, diglycerol, triglycerol, polyglycerols, bis(tri-methylolpropane), tris(hydroxymethyl)isocyanurate, tris(hydroxyethyl)isocyanurate, phloroglucinol, trihydroxytoluene, trihydroxydimethylbenzene, phloroglucide, hexahydroxybenzene, 1,3,5-benzenetrimethanol, 1,1,1-tris(4'-hydroxyphenyl)methane, 1,1,1-tris(4'-hydroxyphenyl)ethane, sugars, for example glucose, sugar derivates, for example sorbitol, mannitol, diglycerol, threitol, erythritol, adonitol (ribitol), arabitol (lyxitol), xylitol, dulcitol (galactitol), maltitol, isomalt, or polyesterol. In addition, B1 may be a trifunctional or higher-functionality polyetherol based on alcohols which have at least three OH groups, and $C_2$-$C_{24}$ alkylene oxide. The polyetherol usually comprises one to 30, preferably one to 20, more preferably one to 10 and most preferably one to eight molecules of ethylene oxide and/or propylene oxide and/or isobutylene oxide per hydroxyl group.

A hyperbranched polyester based on a hydrophobic dicarboxylic acid and a trifunctional alcohol is common knowledge, for example from the pending EP 09179828.0. A suitable hydrophobic dicarboxylic acid is an aliphatic $C_{10}$-$C_{32}$ dicarboxylic acid. Preference is given to sebacic acid, α,ω-undecanedicarboxylic acid, α,ω-dodecanedicarboxylic acid, tridecanedicarboxylic acid (brassylic acid), especially sebacic acid. Another suitable hydrophobic dicarboxylic acid is a dicarboxylic acid having a polyisobutylene group (also referred to hereinafter as "PIB diacid"). Additionally suitable hydrophobic dicarboxylic acids are also succinic acid units having $C_3$-$C_{40}$ groups, preferably substituted succinic acid units of the formula (II)

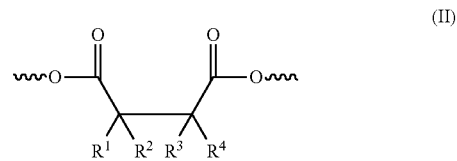

where $R^1$, $R^2$, $R^3$ and $R^4$ are each independently H, a $C_3$ to $C_{40}$-alkyl radical or a $C_3$ to $C_{40}$-alkenyl radical, with the proviso that at least one of the $R^1$, $R^2$, $R^3$ and $R^4$ radicals is not H. The radicals are preferably alkenyl radicals.

Preferably two or three of the $R^1$, $R^2$, $R^3$ or $R^4$ radicals are H, and more preferably three of the radicals are H, i.e. the succinic acid unit has only one alkyl or alkenyl group. The one substituent may be in the $R^1$ or $R^3$ position. Suitable trifunctional alcohols are glycerol, trimethylolethane, trimethylolpropane, bis(trimethylolpropane), pentaerythritol, or an alkoxylated (preferably ethoxylated or propoxylated) derivative thereof. It will be appreciated that it is also possible to use mixtures of a plurality of different trifunctional alcohols. Preferred trifunctional alcohols are glycerol, trimethylolpropane and pentaerythritol. Very particular preference is given to glycerol and trimethylolpropane.

Suitable polar polymers RPP are selected from
PPa) a polymer comprising one polar, ethylenically unsaturated monomer;
PPb) a polymer comprising poly($C_{2-5}$-alkylene oxide), where at least 50 mol % of the $C_{2-5}$-alkylene oxide groups are ethylene oxide; or
PPc) a polycondensate from the group of the polyurethanes, polyesterpolyurethanes, polyetherpolyurethanes, polycarbonates, polyesters and polyamides, where the monomeric units present are poly(ethylene oxide) and/or a polycondensable monomer having at most four carbon atoms.

A preferred polar polymer RPP is the polar polymer PPb.

Preferred polar polymers PPa are polymers comprising a polar, ethylenically unsaturated monomer selected from vinylpyrrolidone, (meth)acrylic acid, a sulfo-containing (meth)acrylate (such as 2-acrylamido-methylpropanesulfonic acid), an amino-functional (meth)acrylate (such as dimethylaminoethyl(meth)acrylate), (meth)acrylic esters of a polyethylene glycol derivative (such as polyethylene glycol monomethyl ether(meth)acrylate), itaconic acid, maleic anhydride, OH-substituted $C_1$-$C_{20}$-alkyl(meth)acrylates (such as hydroxyethyl(meth)acrylate, hydroxypropyl(meth)acrylate), (meth)acrylonitrile, (meth)acrylamide, N-methylol (meth)acrylamide. Preferred polar, ethylenically unsaturated monomers are vinylpyrrolidone, (meth)acrylic acid, polyethylene glycol monomethyl ether(meth)acrylate, and polyethylene glycol(meth)acrylate. The expression "(meth)acrylic" means "acrylic" or "methacrylic". The monomers are normally present in polymerized form in the polymer. PPA may comprise at least one monomer. The proportion of polar monomers is preferably at least 50 mol %, more preferably at least 70 mol %, in relation to all polymerized monomers of PPa. The nonpolar polymer may take the form of a homopolymer or random or block copolymer. The number-average molar mass is usually in the range from 500 to 50 000 g/mol, preferably from 500 to 20 000 g/mol and more preferably from 1000 to 10 000 g/mol. The nonpolar polymer usually comprises at least one functional end group, such as an alcohol, acid, amine, or ester group, preferably introduced via a functional initiator or regulator. Such polymers PPa are typically joined to the focal hydroxyl group by the direct reaction thereof with the functional end group or via a low molecular weight linker, as described hereinafter.

Preferred polar polymers PPb are polymers comprising poly($C_{2-5}$-alkylene oxide), where at least 50 mol %, especially at least 70 mol %, of the $C_{2-5}$-alkylene oxide groups are ethylene oxide. The polymer may take the form of a homopolymer or block polymer. The number average molar mass is usually in the range from 300 to 20 000 g/mol, preferably from 300 to 10 000 g/mol and more preferably from 500 to 5000 g/mol. Such polymers PPb are typically joined to the focal hydroxyl group via a low molecular weight linker, as described hereinafter.

Preferred polar polymers PPc are polycondensates from the group of the polyurethanes, polyesterpolyurethanes, polyetherpolyurethanes, polycarbonates, polyesters and polyamides, the monomer units present being poly(ethylene oxide) and/or a polycondensable monomer having at most four carbon atoms.

Examples of polycondensable monomers having at most four carbon atoms are diacids, diols, diamines or diesters, especially succinic acid, ethylene glycol, 1,3-propylene glycol, 1,4-butanediol, ethylenediamine, 1,4-tetramethylenediamine.

The number average molar mass is usually in the range from 300 to 10 000 g/mol, preferably from 300 to 5000 g/mol and more preferably from 500 to 2000 g/mol. Such polymers PPc are typically joined to the focal hydroxyl group by the direct reaction thereof with the functional end group or via a low molecular weight linker, as described hereinafter.

Preferred polar polymers PPC are polyurethanes, such as polyesterpolyurethanes and polyetherpolyurethanes.

Polyesterpolyurethanes comprise, as hydrophilic sections, polyesterpolyols (also referred to as "polyesterols") in cocondensed form. Polyesterpolyols comprise at least two OH groups and at least two ester groups per molecule; the number-average molar mass $M_n$ of these compounds is preferably at least 400 g/mol. Polyesterpolyols preferred in accordance with the invention have a number-average molecular weight $M_n$ in the range from 400 to 5000 g/mol, more preferably from 400 to 2000 g/mol.

Polyesterpolyols are generally prepared by the reaction of dicarboxylic acids with polyols at high temperature. Details of the industrial scale preparation of polyesterpolyols can be found, for example, in the Kunststoffhandbuch [Plastics Handbook] Polyurethane, published by G. Oertel, 3rd edition 1993, Carl Hanser Publishers, chapter 3.1.2, especially chapter 3.1.2.3.

Polyetherpolyurethanes comprise, as hydrophilic sections, polyetherpolyols in cocondensed form. Polyetherpolyols (also "polyetherols") comprise at least two OH groups and at least two ether groups per molecule, the $M_n$ of these polyetherols being preferably at least 1000 g/mol.

Polyetherpolyols are generally so hydrophilic that they are water-soluble at room temperature (20° C.). The preparation of polyether alcohols is described in M. Ionescu, "Chemistry and technology of polyols for polyurethanes", Rapra Technology, 2005.

Particularly suitable polyetherols are, for example, the polymerization products of ethylene oxide (EO), the copolymerization or graft polymerization products thereof, and the polyethers obtained by condensation of polyhydric alcohols or a mixture thereof and those obtained by ethoxylation of polyhydric alcohols, amides, polyamides and amino alcohols. Examples thereof are, for instance, polyethylene glycols, addition products of ethylene oxide onto trimethylolpropane or EO-propylene oxide (PO) block copolymers. Preference is given to polyols of the general formula HO—$(CH_2$—$CH_2$—$O)_n$—H, where n may assume the values in the range from 30 to 450. The polyetherols preferably possess $M_n$ values in the range from 1500 to 12 000 g/mol, more preferably up to 10 000 g/mol.

Suitable polyisocyanates for the polar polymers PPc comprise preferably an average of 2 to at most 4 NCO groups, particular preference is given to diisocyanates. In one of the preferred embodiments, the inventive polyurethanes comprise cycloaliphatic or aliphatic diisocyanate radicals, more preferably aliphatic diisocyanate radicals. Examples of cocondensed aliphatic diisocyanates include: 1,4-butylene diisocyanate, 1,12-dodecamethylene diisocyanate, 1,10-decamethylene diisocyanate, 2-butyl-2-ethylpentamethylene diisocyanate, 2,4,4- or 2,2,4-trimethylhexamethylene diisocyanate and especially hexamethylene diisocyanate (hexane 1,6-diisocyanate, HDI). Examples of cocondensed cycloaliphatic diisocyanates include: isophorone diisocyanate (IPDI), 2-isocyanatopropylcyclohexyl isocyanate, 4-methylcyclohexane 1,3-diisocyanate (H-TDI) and 1,3-bis(isocyanatomethyl)cyclohexane. It is also possible for H12-MDI or diisocyanates known as "saturated MDI", for example 4,4'-methylenebis(cyclohexyl isocyanate) (alternatively also known as dicyclohexylmethane 4,4'-diisocyanate) or 2,4'-methylenebis(cyclohexyl)diisocyanate, to be present as radicals in the inventive polyurethanes.

In a preferred embodiment of the invention, the inventive compounds are prepared using a greater amount of isocyanate groups compared to the amount of OH groups of the polyols and any chain extenders. If, for example, exclusively diols and diisocyanates are used in addition to the end groups to prepare the inventive compounds, the diisocyanates are used in a molar excess.

Preferred polyetherpolyurethanes comprise polyetherpolyols and polyisocyanates in cocondensed form. The invention thus provides inventive polymers described above, the polymer additionally being a polyetherpolyurethane and comprising a.) at least one polyetherpolyol having at least 2 OH groups and b.) at least one polyisocyanate in copolymerized form. It is preferred that the molar ratio of NCO groups of the polyisocyanate to OH groups of the polyetherpolyol before the polymerization is in the range from 1.2:1 to 2:1, preferably in the range from 1.4:1 to 1.8:1.

A suitable nonpolar dendron $R^{id}$ is a group of the formula (II),

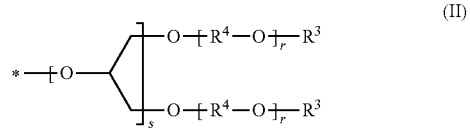

(II)

where
$R^3$: each independently $C_{11}$-$C_{40}$-alkyl, $C_6$-$C_{30}$-aryl, $C_7$-$C_{40}$-aralkyl, or $C_7$-$C_{40}$-alkylaryl, if $R^4$ is ethylene;
$R^3$: each independently H, $C_1$-$C_{40}$-alkyl, $C_6$-$C_{30}$-aryl, $C_7$-$C_{40}$-aralkyl, or $C_7$-$C_{40}$-alkylaryl, if $R^4$ is $C_3$-$C_5$-alkylene;
$R^4$: each independently $C_2$-$C_5$-alkylene;
r: 1 to 200; and
s: 1 to 6.

$R^4$ is preferably independently ethylene, propylene, butylene, pentylene or a mixture of two or more of these groups.

The alkylene radicals of $R^4$ may be present individually or in mixtures of two or more different alkylene radicals. For example, ethylene and propylene radicals may be mixed. The different alkylene radicals may be present in random sequence or in block form.

In one embodiment, $R^4$ is ethylene and $R^3$ is independently $C_{11}$-$C_{40}$-alkyl, $C_6$-$C_{30}$-aryl, $C_7$-$C_{40}$-aralkyl, or $C_7$-$C_{40}$-alkylaryl. If $R^4$ is ethylene, $R^3$ is preferably independently $C_{12}$-$C_{30}$-alkyl, $C_6$-$C_{30}$-aryl, $C_{12}$-$C_{40}$-aralkyl, or $C_{12}$-$C_{40}$-alkylaryl.

In one embodiment, $R^4$ is $C_3$-$C_5$-alkylene and $R^3$ is independently H, $C_1$-$C_{40}$-alkyl, $C_6$-$C_{30}$-aryl, $C_7$-$C_{40}$-aralkyl, or $C_7$-$C_{40}$-alkylaryl.

r is preferably 2 to 100, more preferably 4 to 50 and most preferably 8 to 40.

s is preferably 2 to 5 and more preferably 3 to 4.

A suitable polar dendron $R^{pd}$ is a group of the formula (III),

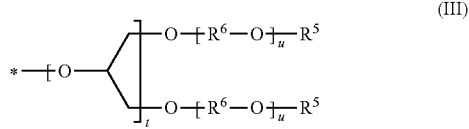

where $R^5$: each independently H, $C_1$-$C_{10}$-alkyl, $-SO_3^{-1}$, $-PO_3^{2-}$, $-COO^-$, $-R'-SO_3^-$, $-R'-PO_3^{2-}$, or $-R'-CO_2^-$, where $R'$ is $C_1$-$C_{12}$-alkylene;

$R^6$: each independently $C_2$-$C_5$-alkylene, where at least 50 mol % of $C_2$-alkylene is present in respect of all $R^6$;

t: 1 to 6; and u: 1 to 200.

$R^5$ is preferably independently H or $C_1$-$C_{10}$-alkyl. $R^5$ is more preferably H or $C_1$-$C_6$-alkyl. $R^5$ is most preferably H or methyl, especially methyl. $R'$ is preferably $C_2$-$C_6$-alkylene.

$R^6$ is preferably independently ethylene, propylene, butylene, pentylene or a mixture thereof, where at least 50 mol % of ethylene is present in respect of all $R^6$. The alkylene radicals of $R^6$ may be present individually or in mixtures of two or more different alkylene radicals. For example, ethylene and propylene radicals may be mixed. The different alkylene radicals may be present in random sequence or in block form.

t is preferably 2 to 5 and more preferably 3 to 4.

u is preferably 2 to 100, more preferably 4 to 50 and most preferably 8 to 40.

The present invention further relates to a process for preparing the inventive amphiphile of the formula (I), comprising the reaction of the focal hydroxyl group of a polar dendron of the formula (IV)

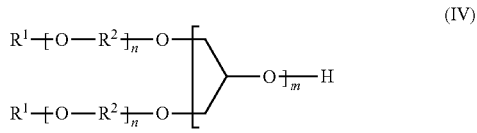

a) with an OH-reactive group of the nonpolar polymer $R^{np}$ or of the polar polymer $R^{pp}$; or b) with an OH-reactive group of a low molecular weight linker which is bonded to the nonpolar polymer $R^{np}$ or the polar polymer $R^{pp}$.

The polar dendron of the formula (IV) may be present in the structure of a dendrimer or a hyperbranched polymer. The polar dendron is preferably a dendrimer. Dendrimers are characterized in that only perfectly branched units without defects are present. It is especially preferred that the structural unit (IV) is a mixture of different dendrimers of different generations, expressed by different parameters m.

Hyperbranched polymers and dendrimers are terms for polymers which are notable for a highly-branched structure and a high functionality. However there are nevertheless clear differences in structure between dendrimers and hyperbranched polymers: dendrimers are molecularly homogeneous macromolecules with a highly symmetric structure. Dendrimers can be prepared proceeding from a central molecule, by controlled stepwise linkage of in each case two or more di- or polyfunctional monomers to each monomer already bound (divergent approach). With each linkage step, this multiplies the number of monomer end groups (and hence of linkages) by a factor of 2 or higher, giving monodisperse polymers built up generation by generation and having tree-like structures, ideally spherical, the branches of which each comprise exactly the same number of monomer units. A further approach consists in linking in the monomers so as to form structures from the periphery until monofunctional, tree-like structures are finally obtained (convergent approach). In this context, "monofunctional" is understood to mean the monofunctionality of the focal unit.

Owing to the branched structure, the polymer properties are advantageous; for example, a surprisingly low viscosity and a high reactivity are observed owing the high number of functional groups at the sphere surface. However, the preparation of the monodisperse dendrimers is generally complicated by the need to introduce protecting groups and remove them again in each linkage step, and the requirement for intensive purifying operations before commencement of each new growth stage, which is why dendrimers are typically prepared only on the laboratory scale.

In contrast, hyperbranched polymers are both molecularly and structurally inhomogeneous, i.e. the molecules of the polymer have a distribution both with regard to the molecular weight and with regard to the structure of the molecule. They are not obtained by generation-by-generation buildup. It is therefore also unnecessary to isolate and to purify intermediates. Hyperbranched polymers can be obtained by simply mixing the components required for formation and the reaction thereof in a one-pot reaction. Hyperbranched polymers may have dendrimeric substructures. In addition, however, they also have linear polymer chains and inhomogeneous polymer branches. A disadvantage of the hyperbranched polymers is that they can be obtained in homogeneously monofunctional form only with very great difficulty, since several focal groups are often incorporated or specifically cocondensed into one and the same macromolecule.

Polar dendrons of the formula (IV) and preparation thereof are common knowledge, for example from the pending European patent application EP 09165576.1. The advantage of these dendrons is that they are preparable in a simple manner without use of protecting groups. Well-defined monofunctional macromolecules are thus obtained via a convergent approach in a multistage process. Optionally, if there is a desire to dispense with separating processes for economic reasons, mixtures of different monofunctional macromolecules are obtained. The mixtures then consist of a plurality of dendrons of different generations (different parameters m).

To prepare these polar dendrons of the formula (IV), at least one compound of the general formula $R^1$—OH is reacted with glycerol or preferably a reactive derivative of glycerol (such as epichlorohydrin, glycidol or glyceryl carbonate), especially with epichlorohydrin. For this purpose, it is preferable to select a molar ratio of compound of the general formula $R^1$—OH to reactive derivative of glycerol, especially epichlorohydrin, such as 2:1. The preparation can be performed for example, at temperatures in the range from 20 to 200° C., preferably at 80 to 130° C. The preparation can be performed in the presence of a catalyst. Suitable catalysts are, for example inorganic and organic bases. If epichlorohydrin is used as the reactive glycerol derivative, the base not only serves as a catalyst but also to neutralize the hydrochloric acid formed. Suitable inorganic bases are, for example, alkali metal carbonates and especially alkali metal hydroxides, such as NaOH and KOH. Suitable organic bases are, for example, tertiary amines, especially triethylamine and [2.2.2]diazabicyclooctane (DABCO), and also pyridine and para-N,N-dimethylaminopyridine. In one embodiment, preparation can be performed in a solvent. Suitable solvents are, for example, ethers, especially 1,4-dioxane, diisopropyl ether, tetrahydrofuran ("THF") and di-n-butyl ether. Further suitable solvents are n-butyl acetate ("butyl acetate"), DMSO, N,N-dimethylformamide ("DMF") and N-methylpyrrolidone, and aromatic solvents, for example toluene.

In embodiments in which water is eliminated in the preparation, it is possible to use desiccating agents, for example molecular sieve, sodium sulfate, magnesium sulfate, or the water formed can be removed by azeotropic distillation. In one embodiment of the present invention, the reaction is performed over a period of 15 minutes to 48 hours, preferably 1 to 24 hours, more preferably 3 to 15 hours.

In one embodiment of the present invention, the reaction is performed in stages, and in as many stages as corresponds to the desired m. This involves adding reactive derivative of glycerol, especially epichlorohydrin, in the number of stages in question. For the stage by stage reaction, the procedure may be, for example, first to react a particular amount of compound of the general formula $R^1$—OH with half the number of moles of glycerol or preferably with a reactive derivative of glycerol, especially with epichlorohydrin. Thereafter, an amount of glycerol or of reactive derivative of glycerol which corresponds to a quarter of the number of moles of compound of the general formula $R^1$—OH is added, and reacted. If it is desired to perform a further stage an amount of glycerol or of reactive derivative of glycerol which corresponds to an eighth of the number of moles of compound of the general formula $R^1$—OH is added thereafter, and reacted. In each further stage, the number of moles of compound of the general formula $R^1$—OH added is reduced correspondingly.

A focal hydroxyl group is understood to mean the single terminal OH group in the hyperbranched polyether of the formula (IV).

A preferred embodiment a) of the inventive preparation comprises the reaction of the focal hydroxyl group of a polar dendron of the formula (IV) with an OH-reactive group of the nonpolar polymer $R^{np}$ or of the polar polymers $R^{pp}$. $R^{np}$ and $R^{pp}$ may comprise an OH-reactive group which can react with the focal hydroxyl group. Preferred OH-reactive groups are a carboxylic anhydride and isocyanate.

A further preferred embodiment b) of the inventive preparation comprises the reaction of the focal hydroxyl group of a polar dendron of the formula (IV) with lactone monomers, alkylene oxide monomers or ethylenically unsaturated monomers, the polymer Rnp or Rpp being prepared from the monomers. Typically, the polymers $R^{np}$ or $R^{pp}$ are obtained proceeding from the focal hydroxyl group of a polar dendron of the formula (IV) by ring-opening polymerization, for example of lactones or alkylene oxides, or by controlled free-radical polymerization of ethylenically unsaturated monomers after an appropriate functionalization of the focal hydroxyl group with a suitable initiator molecule, for example alkylation with 2-bromoisobutyryl bromide.

A further preferred embodiment c) of the inventive preparation comprises the reaction of the focal hydroxyl group of a polar dendron of the formula (IV) with an OH-reactive group of a low molecular weight linker which is bonded to the nonpolar polymer or nonpolar radical $R^{np}$ or to the polar polymer or polar radical $R^{pp}$ in turn via a linker-reactive group.

In general, useful linkers are reactive polyfunctional compounds having at least two reactive groups. Preferred linkers are polyisocyanates having a functionality based on the isocyanate groups of at least 1.5, particularly 1.5 to 4.5 and especially 1.8 to 3.5. Examples are aliphatic, cycloaliphatic and aromatic di- and polyisocyanates, and also the isocyanurates, allophanates, uretdiones and biurets of aliphatic, cycloaliphatic and aromatic diisocyanates. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate and cycloaliphatic diisocyanates, such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups differ in terms of their reactivity, such as toluene 2,4-diisocyanate, toluene 2,6-diisocyanate, cis- and trans-isophorone diisocyanate, or mixtures of these compounds.

Suitable embodiments of the nonpolar polymer $R^{np}$ and of the polar polymer $R^{pp}$ have been described above with regard to the amphiphile of the formula (I). The unoccupied bonding sites described there for the dendrons are bonded to OH-reactive groups in the case of use in the preparation process according to the invention. Suitable OH-reactive groups are carboxylic acids, activated carboxylic acid derivatives (such as carboxylic anhydrides, for example in the form of a succinic anhydride group), carboxylic esters, carbonyl halides, carbonates, epoxides, alpha, beta-unsaturated carbonyl and carboxyl compounds (such as acrylic esters) and isocyanates. Preferred OH-reactive groups are carboxylic anhydrides and isocyanates. The OH-reactive groups are either present directly in the polymers $R^{np}$ or $R^{pp}$, or else in the linkers to be used.

The unoccupied bonding sites described there for the polymers $R^{np}$ and $R^{pp}$ are, in the case of use in the preparation process according to the invention, bonded either directly to the OH groups of the dendrons, for example via carboxylic anhydrides, or indirectly via linker molecules. In the second case, the polymers $R^{np}$ or $R^{pp}$ possess what are called linker-reactive groups. Linker-reactive groups are, for example, hydroxyl groups, carboxyl groups, amino groups, or thiol groups.

Linker-reactive groups can be introduced, for example, by means of a suitable initiator and/or regulator. Alternatively, the linker-reactive group can be introduced in a controlled manner at one or both ends of the chain via a controlled free-radical reaction according to the prior art (such as atom transfer radical polymerization (ATRP), reversible addition fragmentation chain transfer polymerization (RAFT) or nitroxide mediated polymerization (NMP)). It is equally possible that a functional group in the polymer chain is used as the linker-reactive group, for example one of possibly many OH groups in a polymerized hydroxyethyl(meth)acrylate. In the case of a polycondensate, linker-reactive groups can be obtained at the chain ends by virtue of a suitable stoichiometry; for example, it is possible to prepare isocyanate-functionalized polyurethanes and use them in accordance with the invention. By ring-opening polymerization of a lactone, it is possible to obtain a functional hydroxyl group at the chain end in a controlled manner. In the case of a polyalkylene glycol, the linker-reactive group used may be a hydroxyl group at the chain ends.

In the bonding of the polymers $R^{np}$ or $R^{pp}$ to the dendrons via linker molecules, the procedure is usually first to couple the linker to the OH group of the dendron, and then to bond the linker-containing dendron to the linker-reactive group of $R^{np}$ or $R^{pp}$. In a further embodiment, the sequence is reversed. Preference is given to first reacting the less reactive component (for example an OH group) with the linker and then completing the coupling reaction with the more reactive component (for example an amino group).

The process according to the invention for preparing the amphiphile of the formula (I) more preferably comprises the reaction of the focal hydroxyl group of a polar dendron of the formula (IV) with the OH reactive group of an aliphatic isocyanate, aliphatic carboxylic anhydride, or carboxylic anhydride-terminated polyisobutylene, especially with the OH reactive group of an aliphatic carboxylic anhydride, or a carboxylic anhydride-terminated polyisobutylene.

Suitable aliphatic carboxylic anhydrides are alkenylsuccinic anhydride with a $C_{8-44}$-alkenyl radical. Examples are n- or isohexenylsuccinic anhydride, n- or isoheptenylsuccinic anhydride, n- or isooctenylsuccinic anhydride, n- or isooctadienylsuccinic anhydride, n- or isononenylsuccinic anhydride, n- or isodecenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride, 2-dodecenyl-3-tetradecenylsuccinic anhydride. It will be appreciated that it is also possible to use mixtures of different substituted anhydrides. Particularly preferred products are n- or isooctenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride or mixtures of the products mentioned. Very particular preference is given to n- or isohexadecenylsuccinic anhydride, n- or isooctadecenylsuccinic anhydride, or mixtures thereof.

Suitable carboxylic anhydride-terminated polyisobutylenes are polyisobutylenesuccinic anhydride (known as PIB-SAs). The synthesis of PIBSAs is known in the literature as the ene reaction between maleic anhydride and polyisobutenes (for example DE A 43 19 672, EP-A 156 310). In a preferred embodiment, these are 1:1 (mol/mol) reaction products of an ene reaction of a polyisobutene and of the enophile. The polyisobutenes are preferably those which have end groups formed from vinyl isomer and/or vinylidene isomer to an extent of at least 60 mol %. Suitable enophiles are fumaryl chloride, fumaric acid, itaconic acid, itaconyl chloride, maleyl chloride, maleic anhydride and/or maleic acid, preferably maleic anhydride or maleyl chloride, more preferably maleic anhydride. The number-average molecular weight $M_n$ of the PIB acid is preferably at least 100 g/mol, more preferably at least 200 g/mol. In general, the number-average molar mass $M_n$ is up to 5000, and more preferably up to 2000 g/mol. In a particularly preferred embodiment, the PIB acids have a number-average molecular weight $M_n$ of 1000+/−500 g/mol.

The reaction of the focal hydroxyl group of a dendron $R^{nd}$ or $R^{pd}$ with the OH reactive group can proceed at temperatures of 20 to 200° C., preferably at 80 to 150° C. Optionally, it is possible to add organic solvent. Preference is given to adding no solvent. The reaction time is guided by the progress of the reaction. The reaction typically takes 10 min to 72 h, preferably 1 h to 12 h. The molar ratio of the reactants is usually in the range from 1:5 to 5:1, preferably in the range from 1:2 to 2:1, more preferably in the range from 1:1.1 to 1.1:1. According to the OH-reactive group, the person skilled in the art optionally selects a catalyst. For carboxylic anhydride groups as the OH-reactive group, addition of catalyst is not usually necessary. For carboxylic acid groups as OH-reactive groups, it is possible to use titanium(IV) butoxide or dibutyltin dilaurate (DBTL) as the catalyst. For isocyanates as the OH-reactive group it is possible to use DBTL, zinc(II) n-octanoate, zinc(II) 2-ethylhexanoate, zinc(II) neodecanoate, bismuth octanoate, or tertiary amines such as dimethylcyclohexylamine and DABCO, as the catalyst.

The reaction product of the preparation according to the invention can be used further directly or after simple purification, for example in the inventive composition.

The invention further relates to a composition comprising an inventive amphiphile of the formula (I) or an amphiphile which has been prepared by the process according to the invention, and a sparingly water-soluble active ingredient.

The maximum solubility of the active ingredient in water at 20° C. is 10 g/l, preferably 2 g/l, more preferably 0.5 g/l and especially 0.1 g/l. The composition may comprise one or more different active ingredients. Examples of active ingredients are active agrochemical ingredients, active cosmetic ingredients, active pharmaceutical ingredients or food supplements (such as vitamins or carotenoids). Preferred active ingredients are active agrochemical ingredients.

Examples of active cosmetic ingredients are cosmetic oils, flavorings and aromas, vitamins or UV absorbers. Cosmetic oils include peanut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, turpentine oil, melissa oil, juniper oil, lemon oil, anise oil, cardamom oil, camphor oil, etc., or mixtures thereof. UV absorbers include 2-hydroxy-4-methoxybenzophenone, 2,2',4,4'-tetrahydroxybenzophenone, 2,2'-dihydroxy-4,4'-dimethoxybenzophenone, 2,4-dihydroxybenzo-phenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate and 2-isoamyl p-methoxycinnamate, and mixtures thereof.

Examples of flavorings and aromas are as described in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate; and additionally vitamin F, which is understood to mean essential fatty acids, particularly linolic acid, linolenic acid and arachidonic acid.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, anesthetics, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

The term "active agrochemical ingredients" (also referred to hereinafter as pesticides) refers to at least one active ingredient selected from the group of fungicides, insecticides, nematicides, herbicides, safeners and/or growth regulators. Preferred pesticides are fungicides, insecticides and herbicides, especially insecticides. Mixtures of pesticides from two or more of the abovementioned classes can also be used. The person skilled in the art is familiar with such pesticides, which can be found, for example, in Pesticide Manual, 14th Ed. (2006), The British Crop Protection Council, London. Suitable insecticides are insecticides from the class of carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof. Suitable fungicides are fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In one embodiment, the pesticide comprises an insecticide; the pesticide more preferably consists of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenozide and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Very particularly preferred insecticides are fipronil, alpha-cypermethrin, deltamethrin, chlorfenapyr, hydramethylnon and metaflumizone. An especially preferred insecticide is fipronil. In a further embodiment, the pesticide comprises a fungicide; the pesticide preferably consists of at least one fungicide. Preferred fungicides are pyraclostrobin, metconazol and epoxiconazol. In a further embodiment, the pesticide comprises a herbicide; the pesticide preferably consists of at least one herbicide. In a further embodiment, the pesticide comprises a growth regulator; the pesticide preferably consists of at least one growth regulator.

The inventive composition comprises typically 0.1 to 70% by weight of active ingredient, preferably 1 to 60% by weight, especially 3 to 50% by weight, based on the composition. The inventive composition usually comprises 0.01 to 40% by weight, preferably 0.05 to 30% by weight, more preferably 0.1 to 20% by weight, of amphiphile.

The weight ratio of amphiphile to active ingredient is usually in the range from 1:50 to 100:1, preferably 1:5 to 50:1, more preferably 1:2 to 25:1. The active ingredient may be present in dissolved form or in solid particulate form. The active ingredient particles may be crystalline or amorphous. The particle size may be 1 nm to 10 µm.

The composition may be in the form of a solid, solution, emulsion, suspension or suspoemulsion of the active ingredient. The inventive composition is preferably an aqueous composition. In a further preferred embodiment, the inventive composition is a solid, and is more preferably a solid solution. In the case of solid solutions, the active ingredient is typically in amorphous form, dispersed in a polymer matrix. It preferably comprises at least 40% by weight, more preferably at least 60% by weight and especially at least 80% by weight of water. The composition typically comprises at most 99% by weight of water.

The inventive composition may comprise formulating assistants, the selection of the assistants typically being guided by the specific application form and the active ingredient. Examples of suitable formulating assistants are solvents, solid carriers, surfactants (including protective colloids, wetters and stickers), organic and inorganic thickeners, bactericides, antifreezes, defoamers, and optionally dyes and adhesives (for example for seed treatment).

Useful surfactants (adjuvants, wetters, stickers, dispersants or emulsifiers) include the alkali metal, alkaline earth metal, ammonium salts of aromatic sulfonic acids, for example of lignosulfonic acid (Borresperse® products, Borregaard, Norway), phenolsulfonic acid, naphthalenesulfonic acid, (Morwet® products, Akzo Nobel, USA) and dibutylnaphthalenesulfonic acid (Nekal® products, BASF, Germany), and also of fatty acids, alkyl- and alkylarylsulfonates, alkyl ether, lauryl ether and fatty alcohol sulfates, and salts of sulfated hexa-, hepta- and octadecanols, and of fatty alcohol glycol ethers, condensation products of sulfonated naphthalene and derivatives thereof with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

In a preferred embodiment, the active ingredient is a pesticide and the inventive compositions are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition is preferably in the form of an emulsifiable concentrate (EC), of a suspension concentrate (SC), of a water-soluble concentrate (SL), of a solution for seed treatment (LS), or of a redispersible concentrate (DC).

The agrochemical formulation is usually diluted before use in order to produce the so-called tankmix. Useful substances for dilution include mineral oil fractions of moderate to high boiling point, such as kerosene or diesel oil, and also coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, isophorone, highly polar solvents, for example dimethyl sulfoxide, N-methylpyrrolidone or water. Preference is given to using water. It is also possible not to add the amphiphile until the tankmix stage. In this embodiment, the inventive composition is present in the form of a tankmix.

The diluted composition is typically applied by spraying or nebulizing. Immediately before application (tankmix), it is possible to add to the tankmix oils of various types, wetters, adjuvants, herbicides, bactericides, fungicides. These agents can be added to the inventive compositions in a weight ratio of 1:100 to 100:1, preferably 1:10 to 10:1. The pesticide concentration in the tankmix can be varied within relatively wide ranges. In general, it is between 0.0001 and 10%, preferably between 0.01 and 1%. The application rates in the case of application in crop protection, according to the type of effect desired, are between 0.01 and 2.0 kg of active ingredient per ha.

The invention further relates to a process for producing the inventive composition by contacting the amphiphile and the active ingredient. The components can be contacted by commonly known methods, such as mixing, emulsifying or suspending.

The invention further relates to the use of the inventive amphiphile in an agrochemical formulation comprising the amphiphile and a pesticide for controlling phytopathogenic fungi and/or unwanted vegetation and/or unwanted insect or mite infestation and/or for regulating the growth of plants, by allowing the composition to act on the particular pests, their surroundings or the plants to be protected from the particular pests, the soil and/or unwanted plants and/or the crop plants and/or the surroundings thereof. In addition, it is possible to use the inventive composition, especially the agrochemical formulation, to control unwanted insect or mite infestation on plants and/or to control phytopathogenic fungi and/or to control unwanted plant growth, by treating seeds of crop plants with the composition.

The invention further relates to the use of the inventive amphiphile for solubilizing a sparingly water-soluble active ingredient in aqueous solutions. The active ingredient preferably has a maximum solubility in water at 20° C. of 10 g/l. "Solubilization" means that more active ingredient can be brought into solution in the presence of the inventive amphiphile than in the absence thereof under otherwise identical conditions. It is preferably possible to bring at least twice the amount, more preferably at least five times the amount and especially ten times the amount into solution.

Advantages of the present invention are that a high concentration of active ingredient can be brought into solution; that the preparation of the amphiphile is possible in a very simple manner and on the industrial scale; and that the amphiphile itself is water-soluble or water-dispersible. In addition, it is possible to provide amphiphiles without anionic groups, such that there cannot be any unwanted interaction with the active ingredients or other formulation excipients in compositions comprising active ingredient. It is also possible to very finely adjust the polarity of the amphiphile, especially of the polar dendron, via the length of the polyalkylene oxide chain (as formed on the basis of $R^2$ in formula (I)).

The examples which follow are intended to illustrate the invention without restricting it.

EXAMPLES

Methyl polyethylene glycol (MPEG) has a mean molar mass of 350 g/mol and an OH number of 160 mg KOH/g, and is commercially available as Pluriol® A 350 E from BASF SE. PIBSA 1000 describes a polyisobutylene (M=1000 g/mol) with a terminal succinic anhydride group. Alkenylsuccinic anhydride is a commercially available alkenylsuccinic anhydride, where the alkenyl radicals are unsaturated $C_{18}$ units, obtainable as Pentasize® 8 from Trigon Chemie. The OH numbers were measured to DIN 53 240. The acid numbers were measured to DIN EN ISO 2114. GPC was carried out with polymethyl methacrylate (PMMA) as the standard.

Example 1

Synthesis of Polar Dendron D.1

A solution of 600 g (1.714 mol) of methyl polyethylene glycol in 2600 ml of 1,4-dioxane was initially charged. 160 g (2.852 mol) of potassium hydroxide were added while stirring. The mixture was heated to 103° C. and then 79.3 g (0.857 mol) of epichlorohydrin in 100 ml of 1,4-dioxane were added dropwise thereto within 30 min. The mixture was then stirred at 103° C. for 2 h. Subsequently, 39.65 g (0.857 mol) of epichlorohydrin in 100 ml of 1,4-dioxane were metered in at 103° C. within 20 min. The mixture was then stirred at 103° C. for 22 h. The resulting brown, turbid mixture was cooled to room temperature and filtered. Thereafter the dioxane was distilled off. The clear brown product D.1 was characterized by GPC (Mn=885 g/mol, Mw=1288 g/mol, in dimethylacetamide).

Example 2

Synthesis of Polar Dendron D.2

A solution of 500 g (1.429 mol) of methyl polyethylene glycol in 2400 ml of 1,4-dioxane was initially charged. 150 g (2.673 mol) of potassium hydroxide were added while stirring. The mixture was heated to 103° C. and then 66.1 g (0.714 mol) of epichlorohydrin in 100 ml of 1,4-dioxane were added dropwise within 30 min. The mixture was then stirred at 103° C. for 2 h. Subsequently, 33.04 g (0.357 mol) of epichlorohydrin in 100 ml of 1,4-dioxane were metered in at 103° C. within 20 min, and the mixture was stirred at 103° C. for a further 2 h. Thereafter 16.5 g (0.179 mol) of epichlorohydrin in 100 ml of 1,4-dioxane were metered in at 103° C. within 15 min and the mixture was allowed to react further at 103° C. for 20 h. The resulting brown, turbid mixture was cooled to room temperature and filtered. Thereafter the dioxane was distilled off. The clear brown product D.2 was characterized by GPC (Mn=1700 g/mol, Mw=2100 g/mol in dimethylacetamide).

Example 3

Synthesis of Polar Dendron D.3

A solution of 240 g (1.818 mol) of isopropylideneglycerol in 625 ml of 1,4-dioxane was initially charged. 240 g (4.277 mol) of potassium hydroxide were added while stirring. The mixture was heated to 103° C. and then 84.1 g (0.909 mol) of epichlorohydrin in 125 ml of 1,4-dioxane were added dropwise within 30 min. The mixture was then stirred at 103° C. for 2 h. Subsequently, 42.05 g (0.455 mol) of epichlorohydrin in 125 ml of 1,4-dioxane were metered in at 103° C. within 20 min, and the mixture was stirred at 103° C. for a further 2 h. Thereafter 21.03 g (0.227 mol) of epichlorohydrin in 125 ml of 1,4-dioxane were metered in at 103° C. within 15 min, and the mixture was allowed to react further at 103° C. for 20 h. The resulting dark brown, turbid mixture was cooled to room temperature and filtered. Thereafter the dioxane was distilled off. The clear brown product D.3 was characterized by GPC (Mn=655 g/mol, Mw=984 g/mol in dimethylacetamide).

Example 4

Synthesis of Amphiphile A.1

140 g of polymer from Example 1 (OH number: 63 mg KOH/g) and 157 g of polyisobutylenesuccinic anhydride (PIBSA, M=1000 g/mol) were initially charged. The mixture was heated to 140° C. while stirring, stirred over a period of 4 hours and then cooled to room temperature. The acid number was 25 mg KOH/g.

Example 5

Synthesis of Amphiphile A.2

143 g of polymer from Example 2 (OH number: 44 mg KOH/g) and 49 g of $C_{1-8}$-alkenylsuccinic anhydride were initially charged. The mixture was heated to 140° C. while stirring, stirred over a period of 4 hours and then cooled to room temperature. The acid number was 25 mg KOH/g.

Example 6

Synthesis of Amphiphile A.3

150 g of polymer from Example 1 (OH number: 63 mg KOH/g) and 57 g of $C_{1-8}$-alkenylsuccinic anhydride were initially charged. The mixture was heated to 140° C. while stirring, stirred over a period of 6 hours and then cooled to room temperature. The acid number was 49 mg KOH/g.

Example 7

Measurement of the Solubilization of Active Ingredients by Amphiphiles 100 mg of polymer were weighed into a 50 ml beaker and dissolved in 9.900 g of distilled water. Subsequently, in each case 100 mg of active ingredient were weighed into the mixture, in order to obtain an oversaturated solution. The mixture was then stirred at room temperature with the aid of a magnetic stirrer for 24 h. After a rest time of one hour, excess (i.e. unsolubilized) active ingredient was removed by centrifuging. The resulting clear or opaque solution was subsequently analyzed for its active ingredient content by means of UV spectroscopy. The wavelengths of the UV spectroscopy measurement are compiled in table 1. The results are compiled in table 2.

TABLE 1

| Active ingredient | Wavelength of UV measurement [nm] |
|---|---|
| Carbamazepine | 286 |
| Pyrene | 334 |
| Pyraclostrobin | 277 |
| Fipronil | 280 |

TABLE 2

Solubility of active ingredient [mg/l] with OLECH-containing polymers

| Solubility [mg/l] in the presence of | Piroxicam | Carbamazepine | Pyrene | Pyraclostrobin | Fipronil |
|---|---|---|---|---|---|
| No polymer[a] | 21 | 140 | 0.1 | 22.5 | 3 |
| Example 4 (A.1) | 40 | 331 | 91 | 190 | 139 |
| Example 5 (A.2) | 45 | 333 | 77 | 193 | 88 |
| Example 6 (A.3) | 47 | 384 | 83 | 196 | 88 |

[a]noninventive

Example 8

Preparation of Suspension Concentrates

An aqueous suspension concentrate of Fipronil was prepared by mixing and grinding the following components: 96 g/l Fipronil, 32 g/l propylene glycol, 2 g/l bactericide, 38 g/l poly(ethylene glycol-block-propylene glycol-block-ethylene glycol), 4 g/l magnesium aluminum silicate, 35 g/l salt of a phenolsulfonic acid-urea formaldehyde condensation product. The amphiphile from Example 4 (220 g/l) was added after the grinding of the mixture and dissolved while stirring.

The particle size (determined with a Malvern Mastersizer 2000) in the resulting suspension was D90<3.1 μm and D50<1.2 μm. The particle size did not change in the course of storage (2 weeks at 54° C.) and there was no aggregate formation or phase separation. The active ingredient content likewise remains constant during storage.

The true viscosity (Brookfield viscometer, 20° C.) was 134 mPas.

The suspension was tested for its dilution properties in 0.1% and 0.65% dilutions in CIPAC D water at 20° C. After 2 hours of storage at rest, it exhibited virtually no sediment.

The invention claimed is:

1. An amphiphile of the formula (I)

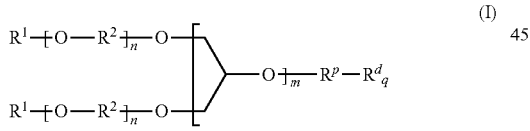

where
R$^1$: each independently H, C$_1$-C$_{10}$-alkyl, —SO$_3$—, —PO$_3^{2-}$, —COO$^-$, —R'—PO$_3^{2-}$, or —R'—CO$_2$—, where R' is C$_1$-C$_{12}$-alkylene;
R$^2$: each independently C$_2$-C$_5$-alkylene, wherein at least 50 mol % of C$_2$-alkylene is present in respect of R$^2$;
n: 1 to 200;
m: 2 to 6;
q: 0 to 50;
R$_p$: a nonpolar polymer R$^{np}$ wherein said R$^{np}$ is NPa or NPb and wherein NPa is —C(O)(CHR$^a$)$_2$—CO$_2$H, where R$^a$ is independently H, C$_4$-C$_{44}$-alkyl, C$_4$-C$_{44}$-alkenyl, C$_6$-C$_{44}$-aryl, C$_7$-C$_{44}$-aralkyl or C$_7$-C$_{44}$-alkylaryl, and wherein at most one of the two R$^a$ radicals is hydrogen; and NPb is —C(O)(CHR$^b$)$_2$—CO$_2$H, wherein R$^b$ is independently hydrogen or a poly(C$_2$-C$_{12}$-alkylene) group, which may optionally comprise at least one carboxylic acid group, a carboxylic anhydride group or an R$^d$ radical bonded via a carboxylic ester group and wherein at most one of the two R$^b$ radicals is hydrogen; and R$^d$: a nonpolar dendron R$^{nd}$.

2. The amphiphile according to claim 1, wherein the nonpolar dendron R$^{nd}$ is a group of the formula (II)

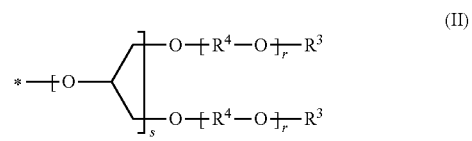

wherein
R$^3$: each independently C$_{11}$-C$_{40}$-alkyl, C$_6$-C$_{30}$-aryl, C$_7$-C$_{40}$-aralkyl, or C$_7$-C$_{40}$ alkylaryl, if R$^4$ is ethylene; each independently H, C$_1$-C$_{40}$-alkyl, C$_6$-C$_{30}$-aryl, C$_7$-C$_{40}$-aralkyl, or C$_7$-C$_{40}$-alkylaryl, if R$^4$ is C$_3$-C$_5$-alkylene;
R$^4$: each independently C$_2$-C$_5$-alkylene;
r: 1 to 200; and
s: 1 to 6.

3. The amphiphile according to claim 2, where R$^1$ is independently H or C$_1$-C$_{10}$-alkyl.

4. A process for preparing the amphiphile of the formula (I) according to claim 1, comprising the reaction of the focal hydroxyl group of a polar dendron of the formula (IV)

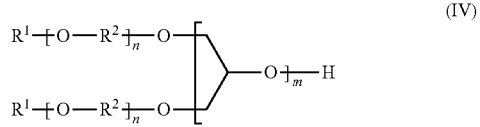

a) with an OH-reactive group of the nonpolar polymer R$^{np}$;
b) with lactone monomers, alkylene oxide monomers or ethylenically unsaturated monomers, the polymer R$^{np}$ being prepared from the monomers; or
c) with an OH-reactive group of a low molecular weight linker which is bonded to the nonpolar polymer R$^{np}$.

5. A composition comprising an amphiphile according to claim 1 and a sparingly water-soluble active ingredient.

6. A method for controlling phytopathogenic fungi and/or unwanted vegetation and/or unwanted insect or mite infestation and/or for regulating the growth of plants, comprising allowing the composition of claim 5 to act on the particular pests, their surroundings or the plants to be protected from the particular pests, the soil and/or unwanted plants and/or the crop plants and/or the surroundings thereof wherein said sparingly water-soluble active ingredient is a pesticide.

7. The method of claim 6, wherein the nonpolar dendron R$^{nd}$ of the amphiphile is a group of the formula (II)

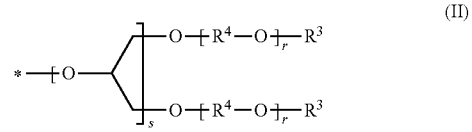

wherein $R^3$: each independently $C_{11}$-$C_{40}$-alkyl, $C_6$-$C_{30}$-aryl, $C_7$-$C_{40}$-aralkyl, or $C_7$-$C_{40}$ alkylaryl, if $R^4$ is ethylene;

$R^3$: each independently H, $C_1$-$C_{40}$-alkyl, $C_6$-$C_{30}$-aryl, $C_7$-$C_{40}$-aralkyl, or $C_7$-$C_{40}$-alkylaryl, if $R^4$ is $C_3$-$C_5$-alkylene;

$R^4$: each independently $C_2$-$C_5$-alkylene;

r: 1 to 200; and s: 1 to 6.

8. The method of claim 6, where $R^1$ of the amphiphile is independently H or $C_1$-$C_{10}$-alkyl.

* * * * *

UNITED STATES PATENT AND TRADEMARK OFFICE
CERTIFICATE OF CORRECTION

PATENT NO.        : 8,841,382 B2                          Page 1 of 1
APPLICATION NO.   : 13/222550
DATED             : September 23, 2014
INVENTOR(S)       : Cristadoro et al.

It is certified that error appears in the above-identified patent and that said Letters Patent is hereby corrected as shown below:

In the Claims

In Claim 1, col. 21, line 53, after "-COO⁻," insert -- -R'-SO$_3^-$, --

Signed and Sealed this
Seventh Day of July, 2015

Michelle K. Lee
*Director of the United States Patent and Trademark Office*